United States Patent
Velis et al.

(10) Patent No.: US 11,324,673 B2
(45) Date of Patent: May 10, 2022

(54) COSMETIC APPEARANCE OF SKIN

(71) Applicant: MIRAKI INNOVATION THINK TANK LLC, Cambridge, MA (US)

(72) Inventors: Christopher Velis, Cambridge, MA (US); Karen Miller, Cambridge, MA (US)

(73) Assignee: MIRAKI INNOVATION THINK TANK LLC, Cambridge, MA (US)

( * ) Notice: Subject to any disclaimer, the term of this patent is extended or adjusted under 35 U.S.C. 154(b) by 0 days.

(21) Appl. No.: 15/682,272

(22) Filed: Aug. 21, 2017

(65) Prior Publication Data
US 2018/0140514 A1    May 24, 2018

Related U.S. Application Data

(60) Provisional application No. 62/424,146, filed on Nov. 18, 2016.

(51) Int. Cl.
| | | |
|---|---|---|
| *A61K 8/04* | (2006.01) | |
| *A61K 8/19* | (2006.01) | |
| *A61K 8/34* | (2006.01) | |
| *A61M 5/19* | (2006.01) | |
| *A61M 5/315* | (2006.01) | |
| *A61M 5/44* | (2006.01) | |
| *A61M 5/46* | (2006.01) | |
| *A61Q 19/08* | (2006.01) | |
| *A61Q 19/06* | (2006.01) | |
| *A61P 17/10* | (2006.01) | |
| *A61K 8/02* | (2006.01) | |

(52) U.S. Cl.
CPC ............ *A61K 8/044* (2013.01); *A61K 8/0204* (2013.01); *A61K 8/19* (2013.01); *A61K 8/345* (2013.01); *A61M 5/19* (2013.01); *A61M 5/3158* (2013.01); *A61M 5/44* (2013.01); *A61M 5/46* (2013.01); *A61P 17/10* (2018.01); *A61Q 19/06* (2013.01); *A61Q 19/08* (2013.01); *A61K 2800/81* (2013.01); *A61K 2800/91* (2013.01)

(58) Field of Classification Search
None
See application file for complete search history.

(56) References Cited

U.S. PATENT DOCUMENTS

| | | |
|---|---|---|
| 3,373,906 A | 3/1968 | Hart et al. |
| 3,605,742 A | 9/1971 | Tibbs |
| 3,893,834 A | 7/1975 | Armstrong |
| 4,363,329 A | 12/1982 | Raitto |
| 4,619,678 A | 10/1986 | Rubin |
| 4,966,601 A | 10/1990 | Draenert |
| 4,983,045 A | 1/1991 | Taniguchi |
| 4,986,079 A | 1/1991 | Koseki et al. |
| 5,143,063 A | 9/1992 | Fellner |
| 5,304,128 A | 4/1994 | Haber et al. |
| 5,445,523 A | 8/1995 | Fischer et al. |
| 5,507,790 A | 4/1996 | Weiss |
| 5,769,879 A | 6/1998 | Richards et al. |
| 6,032,675 A | 3/2000 | Rubinsky |
| 6,041,787 A | 3/2000 | Rubinsky |
| 6,067,803 A | 5/2000 | Wolsey et al. |
| 6,244,052 B1 | 6/2001 | Kasza |
| 6,300,130 B1 | 10/2001 | Toner et al. |
| 6,324,863 B1 | 12/2001 | Henry |
| 6,334,328 B1 | 1/2002 | Brill |
| 6,403,376 B1 | 6/2002 | Toner et al. |
| 6,413,444 B1 | 7/2002 | Kasza |
| 6,430,957 B1 | 8/2002 | Inada et al. |
| 6,458,109 B1 | 10/2002 | Henley et al. |
| 6,475,212 B2 | 11/2002 | Dobak, III et al. |
| 6,547,811 B1 | 4/2003 | Becker et al. |

(Continued)

FOREIGN PATENT DOCUMENTS

| | | |
|---|---|---|
| CN | 102307545 | 1/2012 |
| CN | 103110473 A | 5/2013 |

(Continued)

OTHER PUBLICATIONS

Esposito, 2016, Do you know this syndrom? Type 2 benign symmetric lipomatos (Launois-Bensaude), Brazilian Annals of Dermatology 91:841.
Gentile, 2016, Lipodystrophy in Insulin-Treated Subjects and Other Injection-Site Skin Reactions: Are we Sure Everything is Clear?, Diabetes Therapy 7.
Int Search Report & Written Op dated Dec. 11, 2019, for PCT/US2019/054828, filed Oct. 4, 2019 (8 pages).
Int Search Report & Written Op dated Dec. 23, 2019, for PCT/US19/54834, filed Oct. 4, 2019 (10 pages).

(Continued)

*Primary Examiner* — Robert A Wax
*Assistant Examiner* — Randeep Singh
(74) *Attorney, Agent, or Firm* — Wenderoth, Lind & Ponack, L.L.P.

(57) ABSTRACT

The present invention is directed to targeted delivery of a cold slurry underneath a patient's skin to improve the cosmetic appearance of the skin. The "target" tissue can be muscle tissue that when cooled cannot contract and cause wrinkles/lines in the skin to appear. The target tissue can also be adipose tissue that causes overlying tissue to sag and form wrinkles/lines. The cold slurry induces apoptosis, and reduces the size of the tissue, and causes the connective tissue supporting the skin to thicken and tighten, thereby reducing wrinkles/lines. Skin can also be tightened with cold slurry injected into the dermis layer of the skin or within the layers of the oral mucosa making a cold slurry treatment ideal for reducing the appearance of baggy skin after a patient loses weight and or for treating obstructive sleep apnea. Cold slurry can also be used to treat cellulite and acne.

18 Claims, 9 Drawing Sheets

(56) References Cited

U.S. PATENT DOCUMENTS

| | | | |
|---|---|---|---|
| 6,575,930 B1* | 6/2003 | Trombley, III | A61M 5/142 222/216 |
| 6,673,607 B2 | 1/2004 | Toner et al. | |
| 6,849,072 B2 | 2/2005 | Lee et al. | |
| 6,962,601 B2 | 11/2005 | Becker et al. | |
| 7,118,591 B2 | 10/2006 | Frank et al. | |
| 7,276,051 B1 | 10/2007 | Henley et al. | |
| 7,367,341 B2 | 5/2008 | Anderson et al. | |
| 7,389,653 B2 | 6/2008 | Kasza et al. | |
| 7,422,601 B2 | 9/2008 | Becker et al. | |
| 7,507,234 B2 | 3/2009 | Utley et al. | |
| 7,588,547 B2 | 9/2009 | Deem et al. | |
| 7,603,868 B2 | 10/2009 | Sveinsson | |
| 7,681,411 B2 | 3/2010 | DiLorenzo | |
| 7,699,803 B2 | 4/2010 | Nayak et al. | |
| 7,713,266 B2 | 5/2010 | Elkins et al. | |
| 7,854,754 B2 | 12/2010 | Ting et al. | |
| 8,117,854 B2 | 2/2012 | Lampe et al. | |
| 8,192,474 B2 | 6/2012 | Levinson | |
| 8,275,442 B2 | 9/2012 | Allison | |
| 8,285,390 B2 | 10/2012 | Levinson et al. | |
| 8,298,216 B2 | 10/2012 | Burger et al. | |
| 8,308,681 B2 | 11/2012 | Slocum et al. | |
| 8,337,539 B2 | 12/2012 | Ting et al. | |
| 8,505,315 B2 | 8/2013 | Kasza et al. | |
| 8,523,927 B2 | 9/2013 | Levinson et al. | |
| 8,535,275 B2 | 9/2013 | Salzman | |
| 8,603,073 B2 | 12/2013 | Allison | |
| 8,608,696 B1 | 12/2013 | DiMeo et al. | |
| 8,676,338 B2 | 3/2014 | Levinson | |
| 8,702,774 B2 | 4/2014 | Baker et al. | |
| 8,808,241 B2 | 8/2014 | DiMeo et al. | |
| 8,840,608 B2 | 9/2014 | Anderson et al. | |
| 8,974,451 B2 | 3/2015 | Smith | |
| 9,044,212 B2 | 6/2015 | LePivert | |
| 9,078,634 B2 | 7/2015 | Gonzales et al. | |
| 9,132,031 B2 | 9/2015 | Levinson et al. | |
| 9,314,368 B2 | 4/2016 | Allison et al. | |
| 9,345,526 B2 | 5/2016 | Elkins et al. | |
| 9,375,345 B2 | 6/2016 | Levinson et al. | |
| 9,398,930 B2 | 7/2016 | Leung et al. | |
| 9,408,745 B2 | 8/2016 | Levinson et al. | |
| 9,522,031 B2 | 12/2016 | Anderson et al. | |
| 9,545,523 B2 | 1/2017 | Nanda | |
| 9,585,687 B2 | 3/2017 | Tenenbaum et al. | |
| 9,649,220 B2 | 5/2017 | Anderson et al. | |
| 9,655,770 B2 | 5/2017 | Levinson et al. | |
| 9,656,056 B2 | 5/2017 | Boyden et al. | |
| 9,980,765 B2 | 5/2018 | Avram et al. | |
| 10,174,985 B2 | 1/2019 | Arnitz et al. | |
| 10,406,021 B2 | 9/2019 | Wu et al. | |
| 10,500,342 B2 | 12/2019 | Velis | |
| 2001/0005338 A1 | 6/2001 | Muhlbauer et al. | |
| 2002/0107199 A1 | 8/2002 | Walker | |
| 2003/0012079 A1 | 1/2003 | Coffeen et al. | |
| 2003/0032996 A1 | 2/2003 | Hallman | |
| 2003/0074903 A1 | 4/2003 | Upadhye et al. | |
| 2003/0171715 A1 | 9/2003 | Hommann et al. | |
| 2003/0195463 A1 | 10/2003 | Trombley et al. | |
| 2003/0220674 A1 | 11/2003 | Anderson et al. | |
| 2004/0073280 A1 | 4/2004 | Dae et al. | |
| 2004/0092883 A1 | 5/2004 | Casey et al. | |
| 2004/0199115 A1 | 10/2004 | Rosenman | |
| 2004/0220559 A1 | 11/2004 | Kramer et al. | |
| 2005/0203598 A1 | 9/2005 | Becker et al. | |
| 2005/0251120 A1 | 11/2005 | Anderson et al. | |
| 2006/0036302 A1 | 2/2006 | Kasza et al. | |
| 2006/0161232 A1 | 7/2006 | Kasza et al. | |
| 2006/0190066 A1 | 8/2006 | Worthen | |
| 2007/0005091 A1 | 1/2007 | Zadini et al. | |
| 2007/0010861 A1 | 1/2007 | Anderson et al. | |
| 2007/0056313 A1 | 3/2007 | Kasza et al. | |
| 2007/0106247 A1 | 5/2007 | Burnett et al. | |
| 2007/0198071 A1 | 8/2007 | Ting et al. | |
| 2007/0255362 A1 | 11/2007 | Levinson et al. | |
| 2007/0270925 A1 | 11/2007 | Levinson | |
| 2008/0045880 A1 | 2/2008 | Kjeken et al. | |
| 2008/0077201 A1 | 3/2008 | Levinson et al. | |
| 2008/0077202 A1 | 3/2008 | Levinson | |
| 2008/0077211 A1 | 3/2008 | Levinson et al. | |
| 2008/0161772 A1* | 7/2008 | Nayak | A61M 5/19 604/506 |
| 2008/0183164 A1* | 7/2008 | Elkins | A61B 18/02 606/21 |
| 2008/0195114 A1 | 8/2008 | Murphy | |
| 2008/0236186 A1 | 10/2008 | Kasza et al. | |
| 2008/0287839 A1 | 11/2008 | Rosen et al. | |
| 2008/0300540 A1 | 12/2008 | Lewis | |
| 2009/0012497 A1 | 1/2009 | Uber, III et al. | |
| 2009/0018623 A1 | 1/2009 | Levinson et al. | |
| 2009/0018624 A1 | 1/2009 | Levinson et al. | |
| 2009/0018625 A1 | 1/2009 | Levinson et al. | |
| 2009/0018626 A1 | 1/2009 | Levinson et al. | |
| 2009/0018627 A1 | 1/2009 | Levinson et al. | |
| 2009/0030366 A1 | 1/2009 | Hochman | |
| 2009/0071829 A1 | 3/2009 | O'Banion et al. | |
| 2009/0118722 A1 | 5/2009 | Ebbers et al. | |
| 2009/0125087 A1 | 5/2009 | Becker et al. | |
| 2009/0143765 A1 | 6/2009 | Slocum et al. | |
| 2009/0149929 A1 | 6/2009 | Levinson et al. | |
| 2009/0255276 A1 | 10/2009 | Kasza et al. | |
| 2009/0270814 A1 | 10/2009 | Masi et al. | |
| 2010/0036295 A1* | 2/2010 | Altshuler | A61F 7/00 601/6 |
| 2010/0081971 A1 | 4/2010 | Allison | |
| 2010/0152824 A1 | 6/2010 | Allison | |
| 2010/0152880 A1 | 6/2010 | Boyden et al. | |
| 2010/0249753 A1 | 9/2010 | Gaisser et al. | |
| 2010/0274184 A1 | 10/2010 | Chun | |
| 2010/0280582 A1 | 11/2010 | Baker et al. | |
| 2010/0308257 A1 | 12/2010 | Lampe et al. | |
| 2010/0312202 A1 | 12/2010 | Henley et al. | |
| 2011/0066216 A1 | 3/2011 | Ting et al. | |
| 2011/0190751 A1 | 8/2011 | Ingle et al. | |
| 2011/0238050 A1 | 9/2011 | Allison et al. | |
| 2011/0238051 A1 | 9/2011 | Levinson et al. | |
| 2011/0300079 A1 | 12/2011 | Martens et al. | |
| 2012/0000217 A1 | 1/2012 | Gudnason | |
| 2012/0022518 A1 | 1/2012 | Levinson | |
| 2012/0055187 A1 | 3/2012 | Raines et al. | |
| 2012/0197361 A1 | 8/2012 | Gonzales et al. | |
| 2012/0203312 A1 | 8/2012 | Batzer et al. | |
| 2012/0239123 A1 | 9/2012 | Weber et al. | |
| 2012/0289761 A1 | 11/2012 | Boyden et al. | |
| 2013/0066309 A1 | 3/2013 | Levinson | |
| 2013/0079684 A1 | 3/2013 | Rosen et al. | |
| 2013/0116758 A1 | 5/2013 | Levinson et al. | |
| 2013/0116759 A1 | 5/2013 | Levinson et al. | |
| 2013/0158440 A1 | 6/2013 | Allison | |
| 2013/0158636 A1 | 6/2013 | Ting et al. | |
| 2013/0190744 A1 | 7/2013 | Avram et al. | |
| 2013/0245731 A1 | 9/2013 | Allison | |
| 2013/0253496 A1 | 9/2013 | Anderson et al. | |
| 2013/0319080 A1 | 12/2013 | Sezaki et al. | |
| 2014/0005760 A1 | 1/2014 | Levinson et al. | |
| 2014/0067025 A1 | 3/2014 | Levinson et al. | |
| 2014/0091113 A1 | 4/2014 | Brewster et al. | |
| 2014/0200511 A1 | 7/2014 | Boyden et al. | |
| 2014/0257443 A1 | 9/2014 | Baker et al. | |
| 2014/0277219 A1 | 9/2014 | Nanda | |
| 2014/0277302 A1 | 9/2014 | Weber et al. | |
| 2014/0303608 A1 | 10/2014 | Taghizadeh | |
| 2014/0303696 A1 | 10/2014 | Anderson et al. | |
| 2014/0303697 A1 | 10/2014 | Anderson et al. | |
| 2014/0316393 A1 | 10/2014 | Levinson | |
| 2014/0358079 A1 | 12/2014 | Fischell et al. | |
| 2014/0378937 A1 | 12/2014 | Anderson et al. | |
| 2015/0080769 A1 | 3/2015 | Lotsch | |
| 2015/0112195 A1 | 4/2015 | Berger et al. | |
| 2015/0141916 A1 | 5/2015 | Albrecht et al. | |
| 2015/0216816 A1 | 8/2015 | O'Neil et al. | |
| 2015/0297246 A1 | 10/2015 | Patel et al. | |
| 2015/0320938 A1 | 11/2015 | King et al. | |
| 2015/0328077 A1 | 11/2015 | Levinson | |

(56) References Cited

U.S. PATENT DOCUMENTS

| | | |
|---|---|---|
| 2015/0342780 A1 | 12/2015 | Levinson et al. |
| 2015/0343156 A1 | 12/2015 | Fischell et al. |
| 2016/0051401 A1 | 2/2016 | Yee et al. |
| 2016/0058956 A1 | 3/2016 | Cohn et al. |
| 2016/0081974 A1 | 3/2016 | Lee et al. |
| 2016/0089550 A1 | 3/2016 | DeBenedictis et al. |
| 2016/0112195 A1 | 4/2016 | Jochheim et al. |
| 2016/0128767 A1 | 5/2016 | Azamian et al. |
| 2016/0175141 A1 | 6/2016 | Wu et al. |
| 2016/0184568 A1 | 6/2016 | Harris et al. |
| 2016/0242661 A1 | 8/2016 | Fischell et al. |
| 2016/0317621 A1 | 11/2016 | Bright |
| 2016/0354137 A1 | 12/2016 | Fischell et al. |
| 2016/0354237 A1 | 12/2016 | Gonzales et al. |
| 2017/0035603 A1 | 2/2017 | Kammer et al. |
| 2017/0051353 A1 | 2/2017 | Eng |
| 2017/0105869 A1 | 4/2017 | Frangineas, Jr. |
| 2017/0136237 A1 | 5/2017 | Eckhouse et al. |
| 2017/0143538 A1 | 5/2017 | Lee et al. |
| 2017/0164965 A1 | 6/2017 | Chang et al. |
| 2017/0202613 A1 | 7/2017 | Pellegrino et al. |
| 2017/0246032 A1 | 8/2017 | Gonzales et al. |
| 2017/0274011 A1* | 9/2017 | Garibyan ............... A61K 33/00 |
| 2017/0274078 A1 | 9/2017 | Garibyan et al. |
| 2017/0325992 A1 | 11/2017 | DeBenedictis et al. |
| 2018/0008500 A1 | 1/2018 | Anderson et al. |
| 2018/0116868 A1 | 5/2018 | Velis et al. |
| 2018/0140514 A1 | 5/2018 | Velis et al. |
| 2018/0311079 A1 | 11/2018 | Garibyan et al. |
| 2019/0053939 A1 | 2/2019 | Garibyan et al. |
| 2019/0054242 A1 | 2/2019 | Velis |
| 2019/0070215 A1 | 3/2019 | Perry et al. |
| 2020/0046552 A1 | 2/2020 | Velis et al. |
| 2020/0086054 A1 | 3/2020 | Velis |
| 2020/0113627 A1 | 4/2020 | Alas et al. |
| 2020/0114041 A1 | 4/2020 | Alas et al. |

FOREIGN PATENT DOCUMENTS

| | | |
|---|---|---|
| CN | 105640706 A | 6/2016 |
| CN | 110392561 | 10/2019 |
| EP | 0418979 A2 | 3/1991 |
| EP | 0 445 951 | 9/1991 |
| ES | 2 421 545 | 9/2013 |
| GB | 2 338 428 | 12/1999 |
| JP | 2008-529663 | 8/2008 |
| JP | 2008-545462 | 12/2008 |
| WO | 2006/086479 | 8/2006 |
| WO | 2006/127467 | 11/2006 |
| WO | 2008/101027 | 8/2008 |
| WO | 2009/086399 A2 | 7/2009 |
| WO | 2009/089090 | 7/2009 |
| WO | 2013/113970 | 8/2013 |
| WO | 2016/033380 A1 | 3/2016 |
| WO | 2016033380 A1 | 3/2016 |
| WO | 2016033384 A1 | 3/2016 |
| WO | 2016/054165 | 4/2016 |
| WO | 2016/090175 A1 | 6/2016 |
| WO | 2017/147367 A1 | 8/2017 |
| WO | 2017/196548 A1 | 11/2017 |
| WO | 2018/085212 | 5/2018 |
| WO | 2018/187573 A1 | 10/2018 |

OTHER PUBLICATIONS

Int Search Report & Written Op dated Feb. 11, 2020, for PCT/US19/55633, filed Oct. 10, 2019 (12 pages).
Int Search Report & Written Op dated Jan. 2, 2020, for PCT/US19/55605, filed Oct. 10, 2019 (9 pages).
Int Search Report & Written Opinion dated Jun. 11, 2018, for PCT/US2018/026260, filed Apr. 5, 2018 (6 pages).
Kanamori, 2015, A case of an 8-year-old boy who was strongly suspected of suffering from familial angiolipomatosis, J Pediatric Surg 3.
Kosseifi, 2010, Dercum's Disease: An Unusual Presentation, Pain Medicine 11:1432.
Lv, 2017, A review of the postoperative lymphatic leakage, Oncotarget 8:69069.
Popescu, 2014, Proteus Syndrome: a difficult diagnosis and management plan, J Med and Life 7:1.
Ash, 2003, Chronic peritoneal dialysis catheters: overview of design, placement, and removal procedures, Int Nephrol Dialysis 16(4):323-34.
Brink, 2008, Abdominoplasty with direct resection of deep fat, Plast Reconstructive Surg 123(5):1597-1603.
Ding, 2008, The association between non-subcutaneous adiposity and calcified coronary plaque: A substudy of the multi-ethnic study of atherosclerosis, Am J Clin Nutr 88(3):645-650.
Fox, 2007, Abdominal visceral and subcutaneous adipose tissue compartments—association with metabolic risk factors in the Framingham heart study, Circulation 116:39-48.
Garaulet, 2006, Relationship between fat cell size and number and fatty acid composition in adipose tissue from different fat depots in overweight/obese humans, Int J Obes 30(6):899-905.
Gradinger, 2005, Abdominoplasty, Chapter 83, pp. 2935-3026, in The art of aesthetic surgery: principles & techniques, Nahai, Ed., Quality Med Pub, St. Louis Mo. (92 pages).
International Search Report & Written Opinion dated Aug. 29, 2018 for PCT/US2018/026273 (15 pages).
International Search Report and Written Opinion dated Apr. 12, 2011, for PCT/US11/24766, filed Feb. 14, 2011 (11 pages).
International Search Report and Written Opinion dated May 15, 2018, for PCT/US17/59947, filed Nov. 3, 2017 (8 pages).
International Search Report and Written Opinion dated May 7, 2018, for PCT/US18/20387, filed Mar. 1, 2018 (7 pages).
International Search Report and Written Opinion dated Jun. 11, 2018, for PCT/US2018/026260, filed Apr. 5, 2018 (6 pages).
Laven, 2006, A pilot study of ice-slurry application for inducing laparoscopic renal hypothermia, BJU Int 99:166-70.
Laverson, 2006, Improving abdominoplasty results: reconstruction of the linea alba sulcus by direct excision, Aesthetic Surg J 26:682-6.
Stevens, 2014, Does cryolipolysis lead to skin tightening? A first report of cryodermadstringo, Aesth Surg J 34(6):NP32-NP34.
Yamamoto, 2010, Adipose depots possess unique developmental gene signatures, Obesity 18(5):872-78.
Extended European Search Report dated Sep. 8, 2020 in corresponding European Application No. 17890830.7.
Office Action dated Jul. 13, 2020 in corresponding Mexican Application No. MX/a/2019/005829, with English translation.
Cellulite treatment, "Cellfina", [online], https://www.smartbeautyguide.com/procedures/skin-hair/cellulite-treatment/, retrieved from the internet Aug. 8, 2020.
Friedmann et al., "Cellulite: a review with a focus on subcision", Clinical, Cosmetic and Investigational Dermatology, vol. 10, 2017, pp. 17-23.
Carruthers et al. "Cryolipolysis and Skin Tightening", Dermatol Surg., vol. 40: 12S, December Supplement 2014, pp. S184-S189.
Written Opinion dated Aug. 21, 2020 in corresponding Singapore Application No. 11201904452T.
Extended European Search Report dated Aug. 28, 2020 in European Application No. 17868153.2.
Written Opinion dated Jul. 1, 2020 in Singapore Application No. 11201903946S.
International Preliminary Report on Patentability dated Aug. 21, 2012, for International application No. PCT/US2011/024766, filed Feb. 14, 2011 (8 pages).
Office Action dated Mar. 1, 2021 in Chinese Application No. 2017800786800, with English translation.
Khan et al., "Treatment of cellulite, Part I. Pathophysiology", Continuing Medical Education, J. Am. Acad Dermatol, Mar. 2010, pp. 361-370.
https://www.cellfina.com/how-cellfina-works/, retrieved May 3, 2021.

* cited by examiner

COSMETIC APPEARANCE OF SKIN

CROSS REFERENCE TO RELATED APPLICATIONS

This application claims the benefit under 35 U.S.C. § 119(e) of U.S. Provisional Application Ser. No. 62/424,146 filed on Nov. 18, 2016 the entire disclosure of which is incorporated herein by reference.

BACKGROUND

Many procedures are intended to change the surface appearance of the skin by reducing lines and wrinkles. Some of these procedures involve injecting fillers or stimulating collagen production. More recently, pharmacologically based therapies for wrinkle alleviation and other cosmetic applications have gained in popularity.

Botulinum toxin type A (BOTOX) is an example of a pharmacologically-based therapy used for cosmetic applications. It is typically injected into the facial muscles to block muscle contraction, resulting in temporary paralysis of the muscle. Once the muscle is disabled, the movement contributing to the formation of the undesirable wrinkle is temporarily eliminated. Another example of pharmaceutical cosmetic treatment is mesotherapy, in which a cocktail of homeopathic medication, vitamins, and/or drugs approved for other indications is injected into the skin to deliver healing or corrective treatment to a specific area of the body. Various cocktails are intended to affect body sculpting and cellulite reduction by dissolving adipose tissue, or skin resurfacing via collagen enhancement. Development of non-pharmacologically based cosmetic treatments also continues. For example, endermology is a mechanical based therapy that utilizes vacuum suction to stretch or loosen fibrous connective tissues, which are implicated in the dimpled appearance of cellulite.

While BOTOX and/or mesotherapies can temporarily reduce lines and wrinkles, reduce fat, or provide other cosmetic benefits they are not without their drawbacks, particularly the dangers associated with injection of a known toxic substance into a patient, the potential dangers of injecting unknown and/or untested cocktails, and the like. Additionally, while the effects of endermology are not known to be potentially dangerous, they are brief and only mildly effective.

In light of the above, it would be desirable to provide improved medical devices, systems, and methods, particularly for treatment of wrinkles, fat, cellulite, and other cosmetic defects. It would be particularly desirable if these new techniques provided an alternative visual appearance improvement mechanism which could replace and/or complement known bioactive and other cosmetic therapies, ideally allowing patients to decrease or eliminate the injection of toxins and harmful cocktails while providing similar or improved cosmetic results. It would also be desirable if such techniques were performed percutaneously using only local or no anesthetic with minimal or no cutting of the skin, no need for suturing or other closure methods, no extensive bandaging, and limited or no bruising or other factors contributing to extended recovery or patient "down time".

SUMMARY

The present invention is directed to targeted delivery of a cold slurry underneath a patient's skin to improve the cosmetic appearance of the skin. The appearance of undesirable wrinkles or lines in the skin can be caused by the contractions of muscle tissue that underlie the skin. Tissue that is the target of cold slurry treatment can be a muscle, a nerve that innervates a muscle or a combination of muscle and innervating nerve. Cooling the muscle and/or nerve with the cold slurry can inhibit the muscle from contracting, thereby reducing the appearance of wrinkles or lines. The target tissue can also be adipose tissue that causes overlying tissue to sag and to form wrinkles or lines. The cold slurry cools the adipose tissue and induces apoptosis, which reduces the size of the tissue. The cold temperature simultaneously causes connective tissue supporting the skin to thicken and tighten, thereby reducing the wrinkles or lines. Cold slurry can also be used to treat cellulite and acne.

Skin can also be tightened by way of a cold slurry injection into the dermis layer of the skin or within the layers of the oral mucosa. When injected into loose skin, the cold slurry induces the production of connective tissue around the injection site, which may be due to stimulated collagen production, new elastin formation, fibrosis, or tissue compaction. The skin tightening effect can, for example, reduce the appearance of baggy skin after a patient loses weight. The cold slurry injection is non-invasive and can be done on an out-patient basis making it a convenient way of treating loose skin around a patient's flanks, abdomen, thigh, upper arm, and submental area under the chin, for example. In another example, inducing connective tissue production in the oral mucosa with cold slurry can make the oral mucosa more resistive to collapsing when a patient sleeps. As such, cold slurry is an ideal treatment for obstructive sleep apnea.

The cold slurry can be provided to the target tissue with a delivery device having a cannula. An example of such a device includes a syringe. The cold slurry can be generated within the device itself or within a separate chamber, both of which produce a cold slurry at the point of care using a cooling source and an injectable fluid. Preferably, the cold slurry comprises water, 0.1% to about 20% glycerol, and 0.1% to about 20% salt. The mean temperature of the cold slurry can be about +10° C., about +7° C., about +5° C., about +4° C., about +3° C., about +2° C., about +1° C., about 0° C., about −1° C., about −2° C., about −3° C., about −4° C., about −5° C., about −10° C., about −15° C., about −20° C., about −30° C., about −40° C., or about −50° C. The cold slurry can have ice particles that are preferably spherical or round in shape with a diameter of about 1 mm to about 0.01 mm.

DETAILED DESCRIPTION

The present invention involves delivering a cold slurry to target tissue located beneath the skin. The cold slurry is provided using a delivery device inserted through a subject's skin. The cold slurry cools the target tissue changing the composition of the target tissue and/or in its behavior. Among the most immediate applications of this cold slurry treatment is tightening the subject's skin and the reducing wrinkles and lines as to improve the subject's appearance.

Several examples of the invention involve delivering a cold slurry to immobilize muscles for short treatment of lines and wrinkles. Advantageously, nerves, muscles, and associated tissues can be temporarily immobilized using a cold slurry of moderately cold temperatures of 10° C. to −5° C. without permanently disabling the tissue structures. For long term or permanent treatment, other examples of the invention involve delivering a cold slurry to induce apoptosis in adipose tissues using treatment temperatures from about −1° C. to about −15° C. As such, the longevity and efficacy of such subdermal cold slurry treatments can be selected and controlled, with colder cold slurry temperatures, longer cold slurry treatment times, and/or larger volumes of cold slurry.

Figure 1:
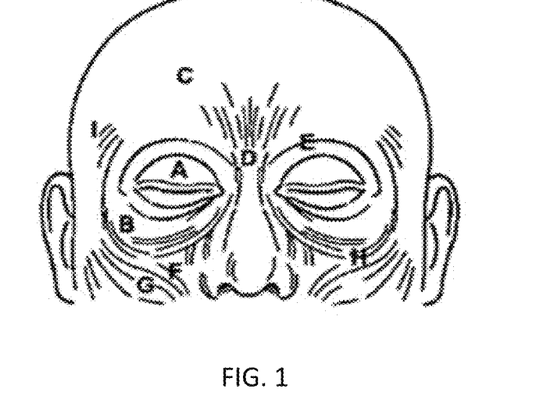
FIGS. 1 and 1A-1L are diagrams of target tissues for cold slurry treatment along with associated lines or wrinkles and treatment patterns.
Figure 1A:
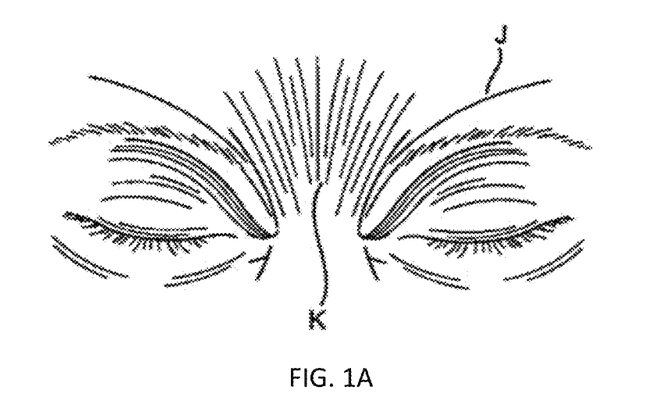
Figure 1B:
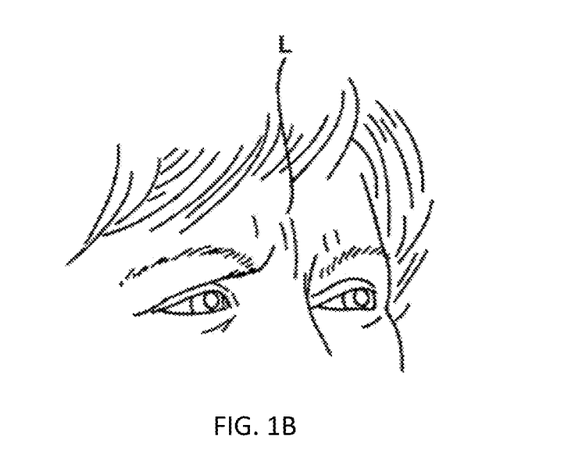
Figure 1C:
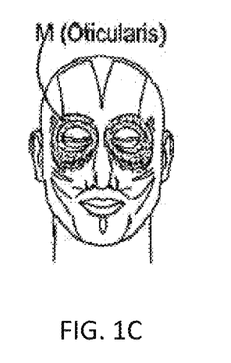
Figure 1D:
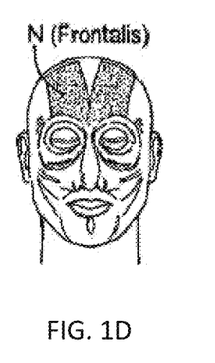
Figure 1E:
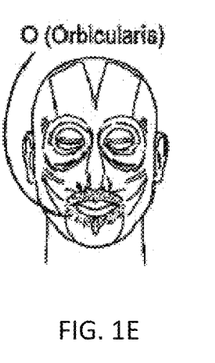
Figure 1F:
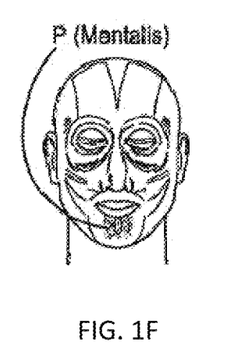
Figure 1G:
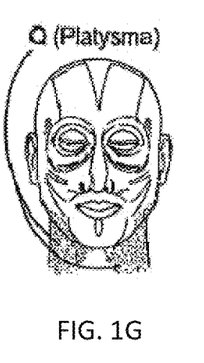
Figure 1H:
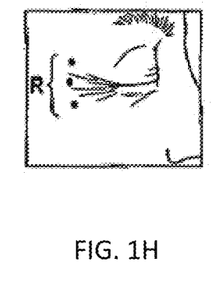
Figure 1I:
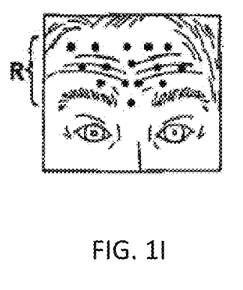
Figure 1J:
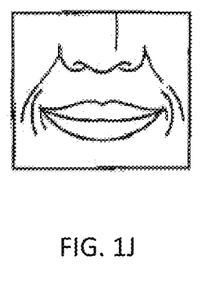
Figure 1K:
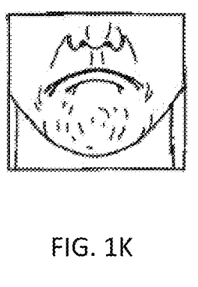
Figure 1L:
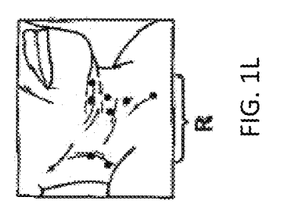
Figure 1M:
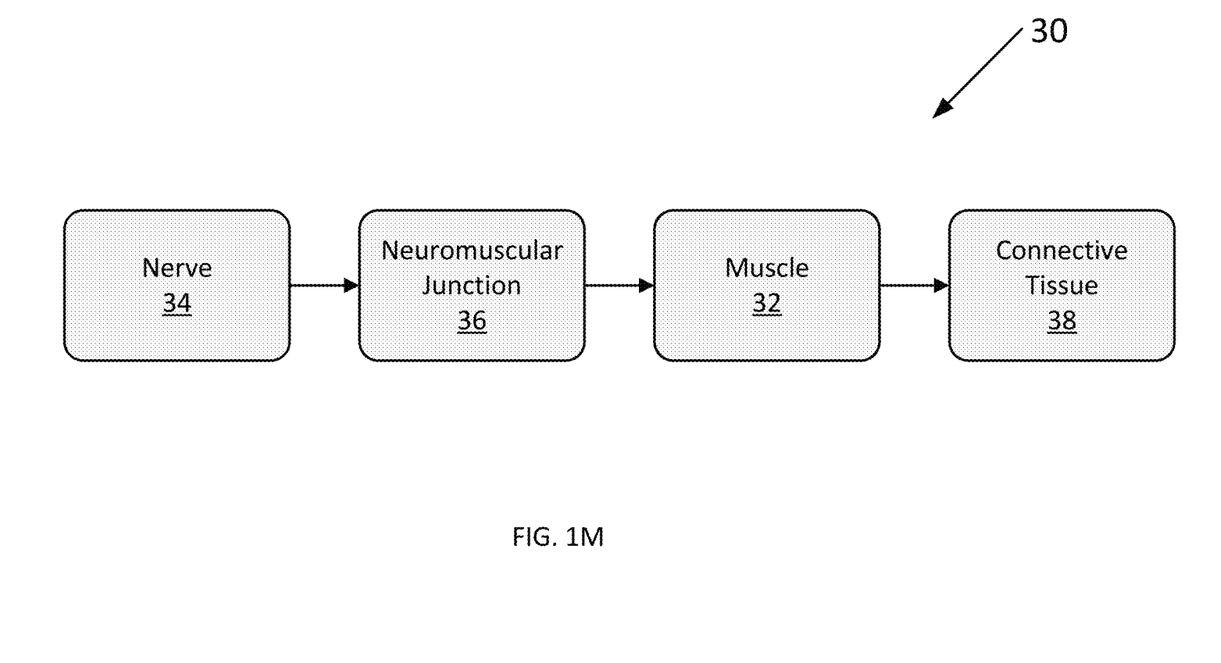
FIG. 1M is a functional block diagram graphically illustrating tissue components included in a contractile chain.

Turning now to FIGS. 1 through 1M, subdermal cold slurry treatment of tissues for alleviating lines and wrinkles can find particular applications for skin surface regions of the face and neck, with procedures optionally being performed so as to alter contractile function of muscles A-I in the upper one-third of the face as shown in FIG. 1. Treatments can be performed so as to alleviate frown lines, lines or wrinkles between the eyes, crow's feet, horizontal lines in the forehead, neck, wrinkles around the mouth, chin, and the like. Many of these cosmetic defects can be treated by targeting and/or inactivating tissues such as the corrugator and/or procerus muscles. More specifically, as seen in FIGS. 1A and 1B, movement of the facial muscles can cause the skin to crease, for example, with contraction of corrugator muscle J and/or procerus muscle K leading to creases between the brows L, which can be clinically referred to as glabellar lines. Additional treatment locations, muscles M-Q whose contractile function can be targeted, related lines or wrinkles, and treatment patterns "R" are illustrated in FIGS. 1C-1L.

Regarding the specific muscles and tissue structures identified in FIG. 1, treatments can be directed towards one or more of levator palpebrae superioris A, orbicularis oculi B, frontalis C, procerus D, corrugator E, levator labii superioris F, zygomaticus major G, zygomaticus minor H, and/or temporalis I. Treatments targeting contraction of oticularis M of FIG. 1C can help decrease crow's feet wrinkles of FIG. 1H, optionally using a treatment pattern R. Treatments altering the function of frontalis N of FIG. 1D can alleviate the wrinkles of FIG. 1I, while altering the function of orbicularis O of FIG. 1E can alleviate the wrinkles shown in FIG. 1J. Wrinkles of the chin as shown in FIG. 1K can be mitigated by treatment of mentalis P and neck wrinkles such as those of FIG. 1L can be improved by treatments of platysma Q, as seen in FIG. 1G. Treatment patterns R for improvement of these and other cosmetic defects can correspond to or be derived from known treatments (such as patterns for injections of BOTOX or the like), can be determined by anatomical analysis using the desired physiological effects, by animal or clinical studies, or the like.

Target muscles for contraction inhibition so as to alleviate wrinkles and the like can often include the glabellar and procerus complex including, but not limited to, the corrugator, procerus, orbicularis oculi, depressor, supercilii, and frontalis. Other muscle groups of the facial region can also be contraction-inhibited, such as the nasalis, orbicularis oris, buccinator, depressor anguli oris, quadratus labii superioris and inferioris, zygomaticus major and minor, platysma, and mentalis. Contraction of these and/or other muscles can be inhibited by targeting associated nerve tissues, connective tissues, nerve/muscle interface, blood supply, and/or at least a portion of tissues of one or more of these muscles themselves. Preferred wrinkle alleviation treatments can alter functioning of muscles including one or more of, but not limited to, frontalis pars medialis, frontalis pars lateralis, corrugator supercilii, procerus, depressor supercilii, levator palpebrae superioris, orbicularis oculi pars orbitalis, orbicularis oculi pars palpebralis, levator labii superioris alaquae nasi, levator labii superioris, zygomaticus minor, zygomaticus major, levator anguli oris (a.k.a. caninus), buccinator, depressor anguli oris (a.k.a. triangularis), depressor labii inferioris, mentalis, incisivus labii superioris, incisivus labii inferioris, risorius, platysma, orbicularis oris, masseter, temporalis, internal pterygoid, digastric (anterior and posterior belly), stylohyoid, geniohyoid, mylohyoid, styloglossus, hyoglossus, genioglossus, sternocleidomastoid, nasalis, maxillae, quadratus labii superioris and inferioris.

In some examples, delivering cold slurry to tissues included in a contractile function chain 30 will affect a desired change in a composition of the treated tissue and/or a change in its behavior which is sufficient to mitigate wrinkles of the skin associated with contraction of a muscle 32, as illustrated in FIG. 1M. While this can involve a cold slurry treatment of the tissues of muscle 32 directly, cold slurry treatments can also target nerve tissues 34, neuromuscular junction tissues 36, connective tissues 38, and the like. Still further tissues can directly receive the cold slurry treatment, for example, with cold slurry treatments being directed to tissues of selected blood vessels so as to induce hypoxia in muscle 32 or the like. Regardless of the specific component of contractile chain 30 which is treated, the cold slurry treatment will preferably inhibit contraction of the muscle 32, which would otherwise form wrinkles or lines in the exposed skin surface overlying that muscle.

A variety of specific tissue cold slurry treatment mechanisms targeting one or more components of contractile chain 30 with cold slurry can be employed so as to inhibit lines or wrinkles. For example, using a cold slurry to ablate muscle cells/tissues, or the associated nerves (optionally being a component thereof integral to nerve function such as a myelin sheath or the like), or the nerve endings or neuromuscular junction (which generally forms the interface between the nerves and the muscles) can be sufficient to inhibit muscular contraction. Such ablation can result in a short-term, long-term or permanent inactivation of the muscle. Other long-lasting or permanent treatments can involve using a cold slurry to induce apoptosis, typically at temperatures which are not as severe as ablation temperatures.

Alternative mechanisms which can be shorter in effect can include using a cold slurry to stun of one or more components of contractile chain 30, inactivation of one or more component, or the like. Cold slurry treatments which effectively block the release of or response to chemicals (such as but not limited to acetylcholine) along the contractile chain 30 can be sufficient to inhibit muscular contraction in response to signals transmitted along the neural pathways, either temporarily or permanently, and can also be employed.

Muscular movement is generally controlled by stimulation of a nerve. The motor unit of the neuromuscular system contains three components: motor neuron (spine), axon (spine to motor endplate), and innervated muscle fibers (endplate to muscle). Treatments directed to one or more of these tissues can be employed.

When cold slurry treatments are intended to inhibit muscle contraction, the treatment can be determined at least in part by the type of muscle being treated (skeletal (striated) or smooth (not striated)). For example, skeletal muscle can have muscle fibers that are innervated by motor neuron, with a single neuromuscular junction lying along a midpoint of muscle fibers, and a single muscle fiber within a motor unit supplied by a single motor neuron and its axon. Each muscle receives one or more nerves of supply, and the nerve generally enters deep into the muscle surface near its origin where the muscle is relatively immobile. Blood vessels typically accompany the nerve to enter the muscle at the neurovascular hilum. Each nerve contains motor and sensory fibers, motor endplates, vascular smooth muscle cells, and various sensory endings and endings in fascia. When the nerve enters the muscle, it breaks off into a plexus running into the various layers of muscle epimysium, perimysium, endomysium each terminating in several branches joining a muscle fiber at the motor endplate. Delivering a cold slurry to one or more of these tissues can be sufficient to temporarily or permanently inhibit muscle contraction.

Examples of the invention can interrupt or disable nerve impulses by disrupting conductivity by eliminating or decreasing charge differences across plasma membranes, either mechanically or chemically; by destroying Schwann cells that insulate the axonal processes speeding up impulse conduction; and/or by repeated injury/healing cycles timed to limited capacity for neuron regeneration.

Immobilization of muscle by disabling any one or a specified combination of components of the connective tissue matrix, either temporarily or permanently can also be employed. Cold slurry treatments targeting connective tissues, such as the fibroblasts, myofibroblasts (which can be responsible for contractility of granulation tissue in healing), collagen, reticulin, elastin, or the like of aponeurotic or tendinous attachment of muscles to bone, fascia, ligaments, or the like can also be advantageous, and which tissue is targeted for cold slurry delivery and/or cold slurry treatment dosage can be selected in response to the condition being treated (for example, when primarily treating cellulite dimples rather than primarily treating contraction-induced lines or wrinkles). Cold slurry treatments of the superficial fascia just beneath the skin can also be employed. To achieve a loss of elasticity in fibrous connective tissue during treatment of cellulite, temperature of the cold slurry can be varied to achieve temporary or permanent changes to the morphology of the collagen and elastin matrix contained within that tissue.

Figure 2:
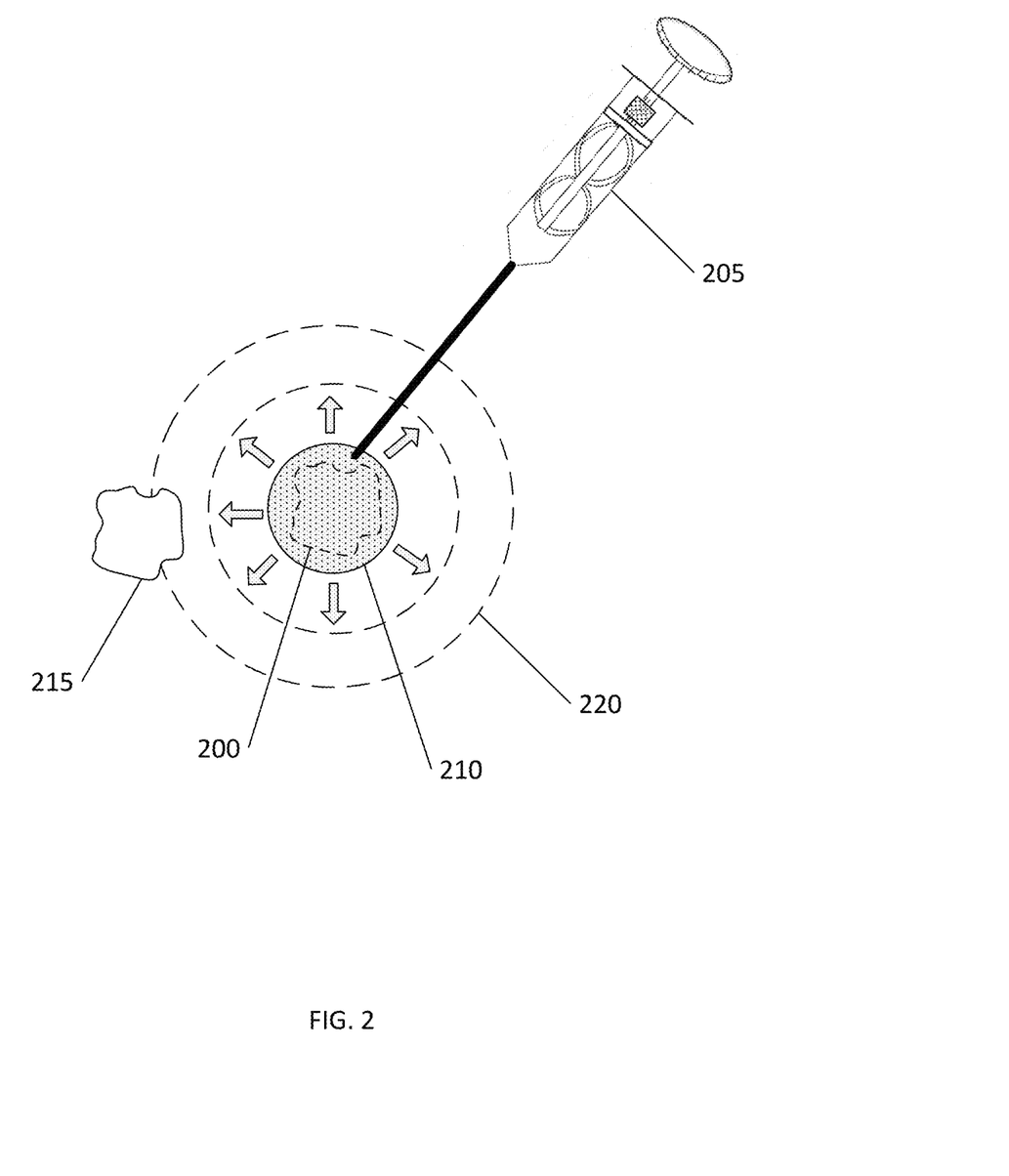
FIG. 2 is a diagram of an example procedure for cooling a target tissue with cold slurry to induce a response in a subject that causes the subject's skin to tighten or reduce wrinkles/lines in the subject's skin.

FIG. 2 shows a target tissue 200 (in phantom line) located underneath a subject's skin. The target tissue 200 can be a muscle tissue located on the subject's face, for example. Contracting the muscle tissue causes a wrinkle to appear on the subject's face. Cold slurry can be delivered to the target tissue 200 from a delivery device 205. (The delivery device 205 and cold slurry are described in greater detail at the end this disclosure.)

The cold slurry, shown in the figure as delivered cold slurry 210, can inhibit the target tissue 200 from contracting by interfering with the contractile chain 30 described above. Unable to contract, the cooled target tissue 200 cannot cause a wrinkle to appear. As described above, the efficacy and longevity of the cold slurry treatment can be controlled, at least in part, by the temperature of the cold slurry and the amount of cold slurry that is delivered. Where the cold slurry is placed relative to the target tissue 200 can also affect the treatment.

The tissue being targeted for cold slurry treatment can also be an adjacent tissue 215 near the delivered cold slurry 210. After delivery, the affected area 220 expands to a size larger than the initial delivery site (shown in the figure as arrows radiating outwardly from the delivered cold slurry 210 and dashed circles of increasing size). The affected area 220 reaches a size encompassing the adjacent tissue 215 and the coldness of the delivered cold slurry 210 can inhibit the adjacent tissue 215.

An amount of cold slurry can be delivered to multiple sites at (or near) the target tissue 200. Beneficially, this increases the amount of target tissue 200 that is exposed to the cold slurry and cooled, and can improve the effectiveness of the treatment. The cold slurry can be sterile and biocompatible; and, as such, the delivered cold slurry 210 can be advantageously left in the body (e.g. no removal of the slurry is necessary after cooling has been effected).

Figure 3A:
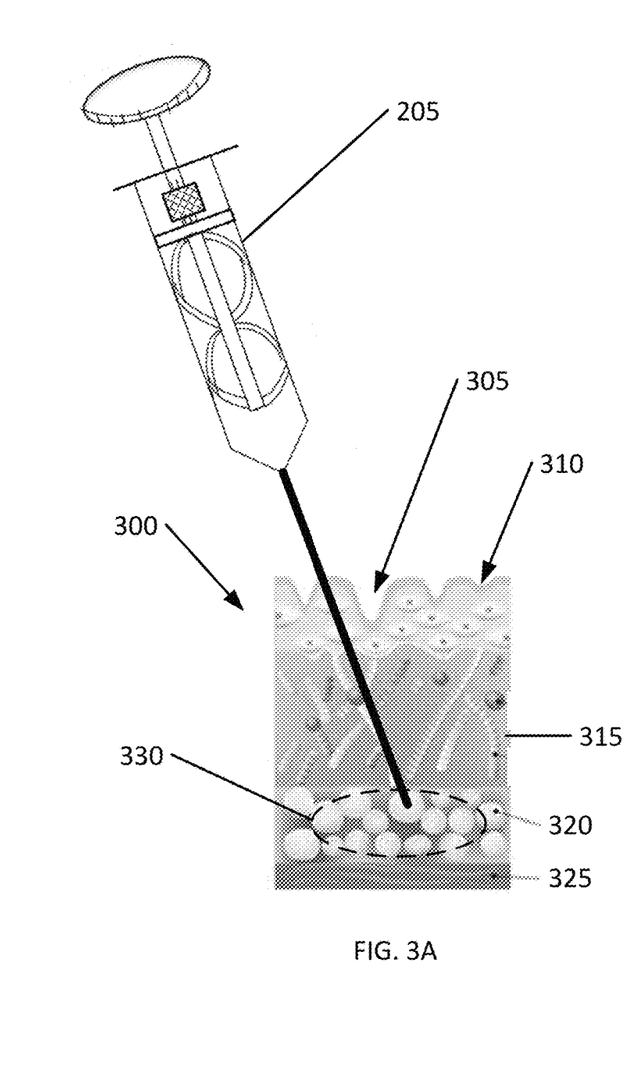
FIGS. 3A and 3B are diagrams of an example procedure for using a cold slurry to induce apoptosis in adipose tissue underlying the subject's skin to tighten the skin or reduce wrinkles/lines in the skin.

FIG. 3A shows a section of a subject's skin 300 having a wrinkle 305 and a line 310. The tissues underlying the skin 300 include connective tissue 315, adipose tissue 320, and muscle tissue 325. The connective tissue 315 is made up of collagen and elastin. Collagen is a vital fibrous protein that is found all throughout the body; it connects and supports tissues including skin, bone, muscles, tendons, cartilage and organs. Collagen is the main protein in connective tissue and is responsible for skin firmness and suppleness. Elastin is another protein in connective tissue that is responsible for giving structure to skin and organs. It allows the skin 300 to resume shape after stretching or contracting. Together, collagen and elastin keep the connective tissue 315 firm and help it to hold its shape. As the skin 300 loses collagen, it loses elasticity and wrinkles and fine lines appear.

In an example procedure for reducing the wrinkle 305 and line 310, a practitioner inserts a cannula of the delivery device 205 through the skin 300 and the connective tissue 315 until the cannula reaches the adipose tissue 320, i.e., the target tissue. In a convenient example, the procedure is performed using a syringe. The practitioner then delivers a cold slurry from the delivery device to the adipose tissue 320. The cold slurry, shown in the figure as delivered cold slurry 330, cools the adipose tissue 320 and triggers apoptosis.

Figure 3B:
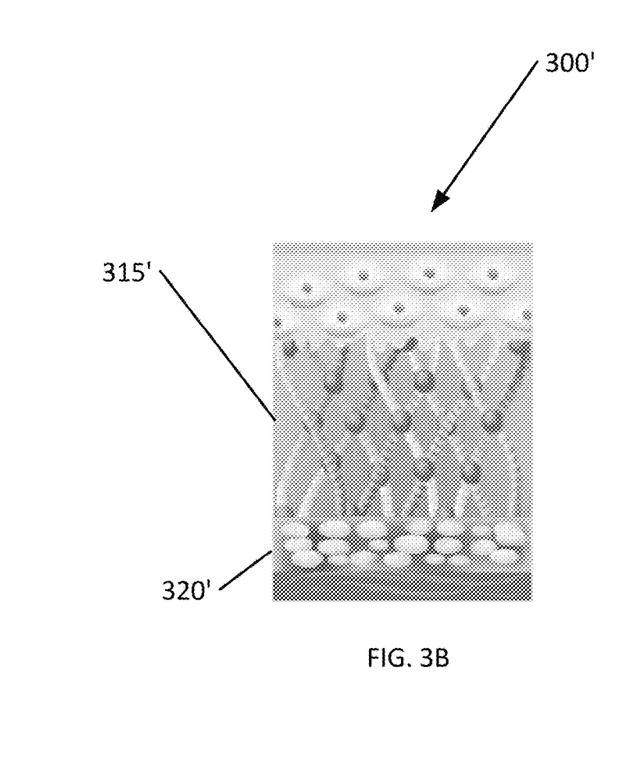

Apoptosis triggers macrophages to remove adipocytes from the adipose tissue 320 and reduces the size of the tissue. The cold slurry simultaneously causes connective tissue 315' supporting adipose tissue 320' to become thicker, as shown in FIG. 3B. Adipose tissue is generally mobile and weakly supportive. The relative increase in the connective tissue 315' after the procedure provides better support for the adipose tissue 320'. As a result, skin 300' tightens and reduces the wrinkle and line, as shown in FIG. 3B. This procedure can used to tighten skin located around the subject's flanks, abdomen, thigh, submental area and upper arm, for example.

Another application for subdermal delivery of cold slurry is to tighten skin that becomes loose with fat loss, for example around the belly. Removing fat using conventional techniques, such as liposuction, results in there being excess skin where the fat is removed and leaves the skin looking "baggy". The bagginess can be reduced by surgically removing the excess skin but this adds more time to the procedure and increases recovery time. Advantageously, the cold slurry approach can both remove fat and tighten loose skin caused by the loss of fat, thereby reducing the appearance of baggy skin.

Figures 4A, 4B:
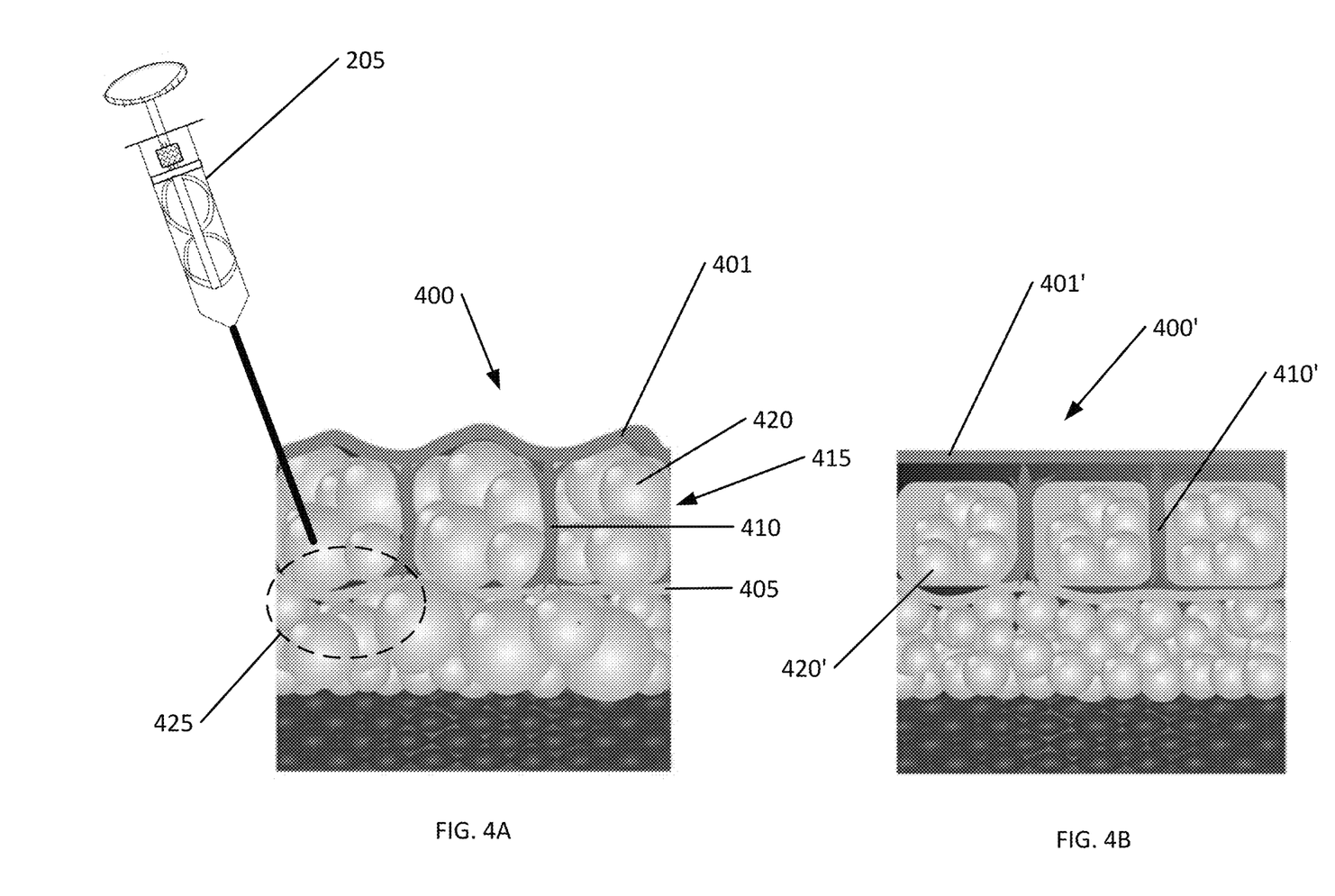
FIGS. 4A and 4B are diagrams of an example procedure for using a cold slurry to treat cellulite.

Yet another application for subdermal delivery of cold slurry is to treat cellulite (also known as adiposis edematosa, dermopanniculosis deformans, status protrusus cutis, gynoid lipodystrophy, and orange peel syndrome). Cellulite is the appearance of an unattractive dimpled skin or "dimpled fat" on the outer thighs, buttocks, and other areas of the body where fat is found in close proximity to the skin. FIG. 4 shows cellulite 400, including skin 401 connected to deeper tissue layers 405 by vertical fibrous tissue strands 410. The vertical fibrous tissue strands 410 create separate compartments 415 containing fat (adipose) cells 420. When fat cells 420 increase in size, these compartments 415 bulge and produce a waffled (orange peel) appearance of the skin 401. This is because the vertical fibrous tissue strands 410 are inelastic compared to the fat cells 420.

The fat cells 420 in the cellulite 400 are the same like the fat cells found elsewhere in the body. In an example procedure for treating cellulite, a practitioner inserts a cannula of the delivery device 205 through the skin 401 until the cannula reaches the compartment 415 with the fat cells 420, i.e., the target tissue. In a convenient example, the procedure is performed using a syringe. The practitioner then delivers a cold slurry from the delivery device to the fat cells 420. The cold slurry, shown in the figure as delivered cold slurry 425, cools the fat cells 420 and triggers apoptosis. The injection from the cold slurry can also disrupt the vertical fibrous tissue strands 410, and reduce or eliminate their rigidity. Advantageously, as shown in FIG. 4B, the cold slurry approach can reduce/remove fat cells (e.g., reduced fat cells 420') from cellulite 400', tighten overlying skin 401', and disrupt vertical fibrous tissue strands 410', thereby minimizing the dimple appearance of the cellulite 400'.

The treatment of acne is still yet another application for subdermal delivery of cold slurry. Acne is the most common skin disorder that can cause temporary and permanent disfigurement. Typically acne appears on the face, back and/or chest. Acne is a disorder of hair follicles, in which a plug forms within the outflow tract of the hair follicle. Sebum, an oily product of sebaceous glands attached to each hair follicle, and cellular debris builds in the plug. Inflammation and often rupture of the hair follicles ensues, leading to gross inflammation, pus (a "whitehead"), pain, bleeding, and/or eventually scarring. If the acne lesion consists of an accumulated unruptured plug within the hair follicle, a "blackhead" forms. If the follicle ruptures superficially, a small pustule forms that often heals after a few weeks without scarring. If the follicle ruptures within the mid or deep dermis, a painful cystic abscess forms. Cystic acne usually heals with permanent and disfiguring scars.

The amount of sebum excreted by the sebaceous gland is influenced by several major factors, including the size of the sebaceous gland. The larger the gland, the more sebum excreted, and vice versa. The size of the gland changes with age. Prior to puberty, the sebaceous gland is small, and little sebum is excreted. At puberty there is a great increase in sebum excretion which continues through adolescence, after which no further significant change takes place until late in life. Severe acne can leave scars that last a lifetime.

Figure 5:
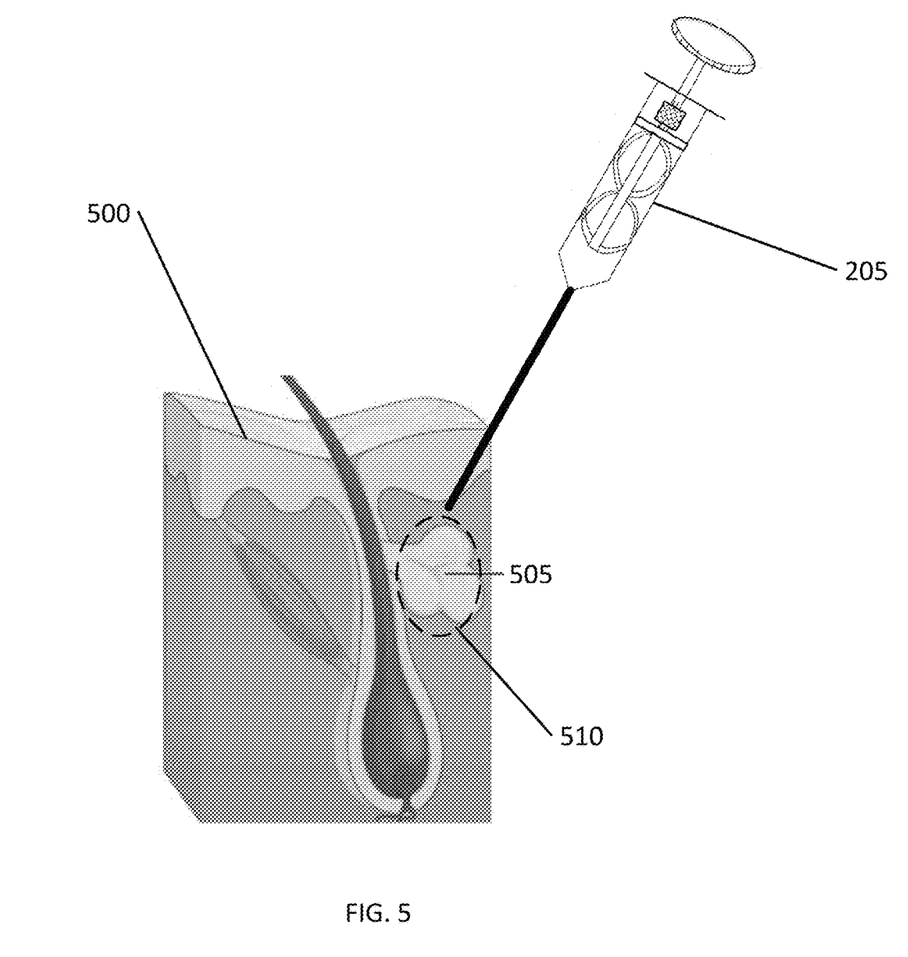
FIG. 5 is a diagram of an example procedure for using a cold slurry to treat acne.

Delivering a cold slurry at or near a sebaceous gland to reduce its activity (i.e., produce less sebum) or to destroy it can be an effective treatment for acne. In an example procedure for treating acne, a practitioner inserts a cannula of the delivery device 205 through skin 500 until the cannula is at or near sebaceous gland 505, i.e., the target tissue. In a convenient example, the procedure is performed using a syringe. The practitioner then delivers a cold slurry from the delivery device 205 to the sebaceous gland 505. The cold slurry, shown in the figure as delivered cold slurry 510, cools the sebaceous gland 505 thereby disrupting the sebocyte cell membrane and alkaline phosphatase activity. The coolness from the delivered cold slurry 510 also reduces sebocyte lipid content, thereby reducing/destroying the activity of the sebaceous gland 505. Beneficially, the targeted delivery of cold slurry can cause preferential injury to sebaceous glands with minimal injury to surrounding tissues.

The cold slurry treatment can also be selective to treating one kind of sebaceous gland over another kind of sebaceous gland, e.g., an old sebaceous gland contrasted with a new sebaceous gland. The selectivity of the treatment can be controlled by varying the temperature of the cold slurry. For example, a cold slurry at a first temperature is selected for treating a first kind (group) of sebaceous gland and a second temperature, different than the first temperature, is selected for treating a second kind (group) of sebaceous gland. This is particularly advantageous when some remaining activity of a sebaceous gland is desirable.

While the cold slurry treatments, above, are described separately, they can be combined to tighten skin and/or to reduce wrinkles and lines. For example, cold slurry can be delivered to adipose tissue where it induces apoptosis. The cold slurry can migrate from the adipose tissue to the underlying muscle tissue and inhibit muscle contractions. Advantageously, delivering the cold slurry can have the combined effect of inhibiting muscle tissue and reducing adipose tissue; and can increase the effectiveness of the treatment. In another example, the cold slurry treatment is combined with a collagen recruitment technique to tighten skin on various parts of the body. In another example, the cold slurry treatment has the combined effect of reducing tissue size and causing an inflammatory response in surrounding tissue or structure, which in turn promotes collagen recruitment. These effects are synergistic and beneficial to tighten skin on various parts of the body.

As previously described, the delivery device 205 of FIG. 2 can be used to deliver cold slurry to a target tissue. In more detail, the delivery device 205 is capable of providing continued agitation to the cold slurry at the point of care, such as through rotation of blades within the delivery device 205, use of vibration, or both. The cold slurry can be cooled/kept cool inside the delivery device 205 through the use of a small profile cooling sleeve that easily slips over the delivery device 205 and provides cooling at the point of care. The cooling sleeve can cool or maintain the temperature of the cold slurry through a number of mechanisms, such as the provision of a refrigerant, the triggering of an endothermic reaction, and/or the compression of gas. Other examples of the delivery device are described in U.S. Provisional Application No. 62/416,484 filed on Nov. 2, 2016, which is incorporated herein in its entirety.

The cold slurry can be made from any sterile, biocompatible fluid that is capable of being cooled to provide a cold slurry. The cold slurry can be generated in the delivery device 205 itself by providing the fluid to the delivery device 205 and cooling the fluid within the delivery device 205 while agitating the fluid. The cold slurry can also be produced in a separate chamber and then transferred to the delivery device 205. Other examples of devices for making cold slurry and methods for making cold slurry are also described in U.S. Provisional Application No. 62/416,484.

Preferably, the temperature of the fluid is cooled to or below about 10° C., 7° C., 5° C., 4° C., 3° C., 2° C., 1° C., 0° C., −1° C., −2° C., −3° C., −4° C., −5° C., −10° C., −15° C., −20° C., −30° C., −40° C., and −50° C. The cold slurry generated has a plurality of sterile ice particles and is suitable for delivery into a subject. Example slurry compositions, slurry temperatures, and cross-sectional dimensions of ice particles are provided in PCT/US2015/047292, which is incorporated herein in its entirety. It is to be understood that an advantage of the cold slurry in accordance with the present invention is that the composition of the cold slurry is suitable to delivery to tissues within the body, such that the slurry can be delivered to a tissue within the body of a patient and remain within the body (e.g. no removal of the slurry is necessary after cooling has been effected).

Skin tightening can occur via cold slurry injection into the dermis layer of the skin, or within the layers of the oral mucosa, which includes the keratinized or nonkeratinized squamous epithelium, the basement membrane, or the lamina propria. This injection can lead to an increase in connective tissue production around the injection site.

The cold slurry treatment acts as an aid to metabolic function by reducing the body's inflammatory reaction to injury, as well as promoting enriched blood flow to the sites of treatment. Injection of cold slurry into the dermis layer of the skin or into the oral mucosa causes vasoconstriction of local blood vessels in order to maintain core body temperature. When external temperature normalizes, rapid dilation of the blood vessels occurs, leading to the elimination of waste and toxins, while oxygenated blood, enriched with vitamins and nutrients, enters the vessels and promotes local collagen and elastin production in tissue structures. This process can be attributed to fibroblasts, which are stimulated by macrophages as an immune response, which subsequently lay down connective tissue at the site of intervention.

Figures 6A, 6B:
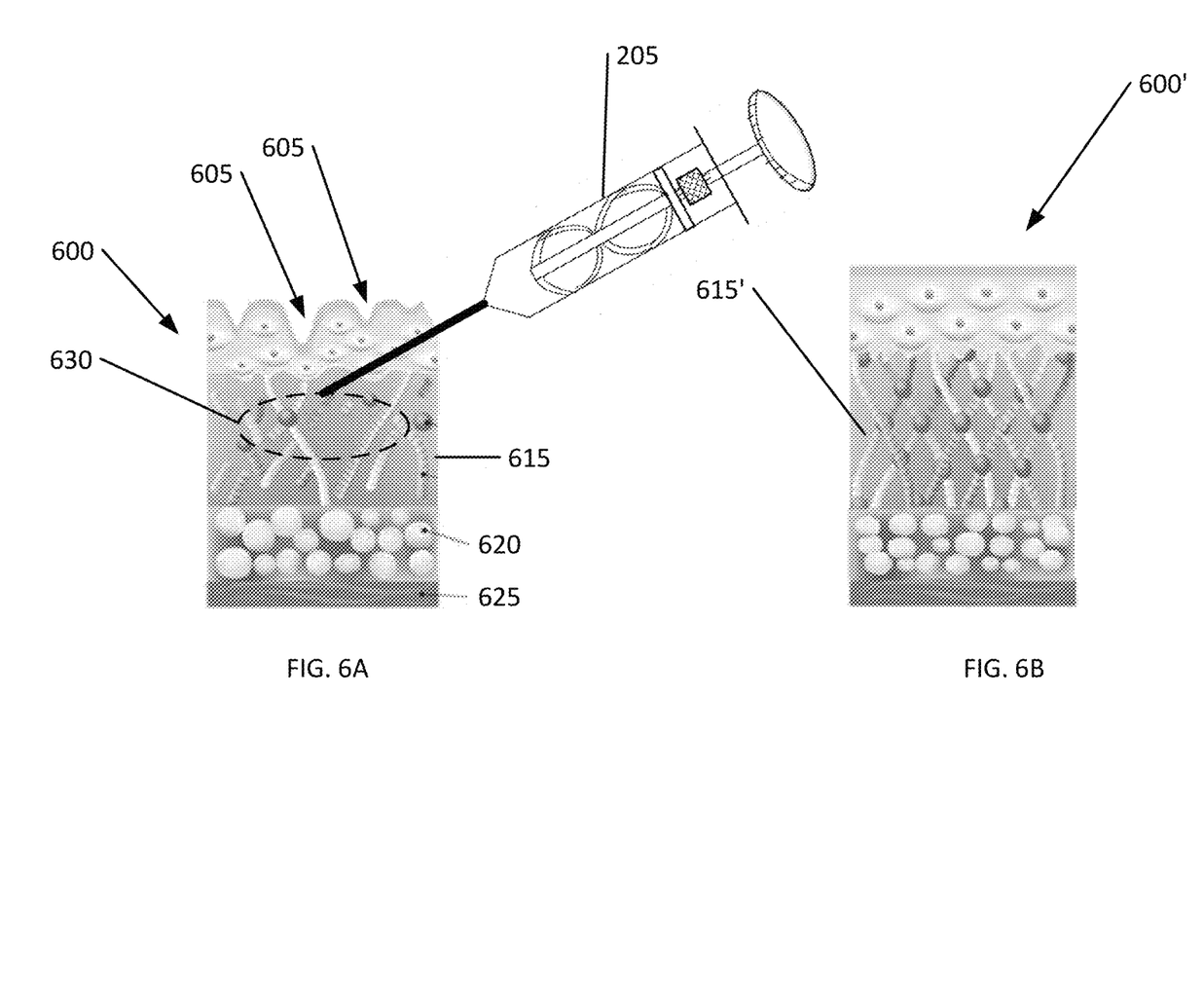
FIGS. 6A and 6B are diagrams of an example procedure for delivering a cold slurry into the dermis layer to tighten skin.

FIG. 6A shows a section of a subject's skin 600 that is loose. The skin 600 can become loose or lax after the subject loses weight, for example. This laxity can give the skin 600 a baggy appearance with folds 605 between the excess skin that is undesirable. The tissues underlying the skin 600 include connective tissue 615, adipose tissue 620, and muscle tissue 625. The connective tissue 615 (also referred to as the dermis) is made up of collagen and elastin. Collagen is a vital fibrous protein that is found all throughout the body; it connects and supports tissues including skin, bone, muscles, tendons, cartilage, and organs. Collagen is the main protein in connective tissue and is responsible for skin firmness and suppleness. Elastin is another protein in connective tissue that is responsible for giving structure to skin and organs. It allows the skin 600 to resume shape after stretching or contracting. Together, collagen and elastin keep the connective tissue 615 firm and help it to hold its shape.

In an example procedure for tightening the skin 600, for example, the submental area around the chin, a practitioner inserts a cannula of the cold slurry delivery device 205 (described above with reference to FIG. 2) through the skin 600 and into the connective tissue 615, i.e., the target tissue. In a convenient example, the procedure is performed using a syringe. The practitioner then delivers a cold slurry from the delivery device 205 to the connective tissue 615. The cold slurry, shown in the figure as delivered cold slurry 630, cools the connective tissue 615. This in turn causes connective tissue 615' to become thicker, as shown in FIG. 3B. As a result, the skin 600' tightens, thereby reducing the appearance of folds. This procedure can used to tighten skin located around the subject's flanks, abdomen, thigh, and upper arm, for example.

In a convenient example, a practitioner uses a cold slurry delivery device having a short bevel needle cannula or syringe for an intracutaneous delivery of cold slurry. The practitioner stretches the skin 600 and orientates the bevel of the needle cannula or syringe upwardly. The practitioner inserts the needle cannula or syringe into the skin 600 at an angle varying from around 10-15 degrees relative to the plane of the skin 600 to form a blister and then delivers a volume of cold slurry into the blister.

Figure 7A:
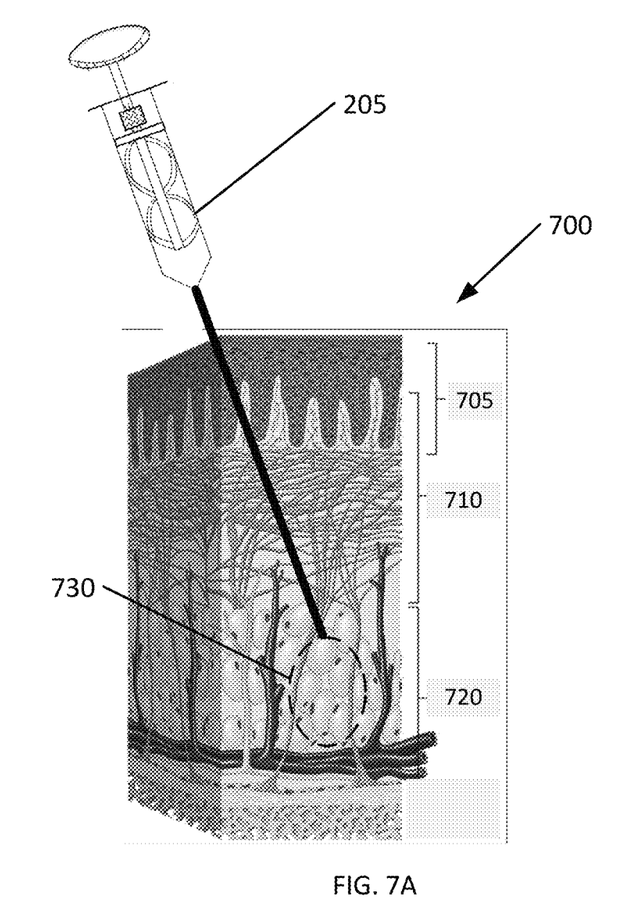
FIG. 7A is a diagram of an example procedure for delivering a cold slurry into the submucosa of the oral mucosa to tighten the oral mucosa.

FIG. 7A shows oral mucosa 700 that lines the back of a subject's throat. The oral mucosa 700 is the mucous membrane lining the inside of the mouth and consists of stratified squamous epithelium called oral epithelium 705 and underlying connective tissue called lamina propria 710. In the back of the throat, the lamina propria 710 overlies submucosa 720. The submucosa 720 includes adipose tissue as shown in the figure. The oral mucosa 700 can be come become lax and collapse during sleep resulting in obstructive sleep apnea.

In an example procedure for tightening the oral mucosa 700 to treat obstructive sleep apnea, a practitioner inserts a cannula of the delivery device 205 (described above with reference to FIG. 2) through the oral epithelium 705 and the lamina propria 710 until the cannula reaches the submucosa 720, i.e., the target tissue. In a convenient example, the procedure is performed using a syringe. The practitioner then delivers a cold slurry from the delivery device 205 to the submucosa 720. The cold slurry, shown in the figure as delivered cold slurry 730, cools the submucosa 720 and triggers apoptosis.

Apoptosis removes adipocytes from the submucosa 720 and reduces the size of the tissue. This in turn causes the lamina propria 710 supporting the submucosa 720 to become thicker. The submucosa 720 is generally mobile and weakly supportive. The relative increase in the lamina propria 710 after the procedure provides better support for the submucosa 720. As a result, the oral mucosa 700 tightens, and reduces the likelihood of it collapsing while the subject sleeps and causing obstructive sleep apnea.

Figure 7B:
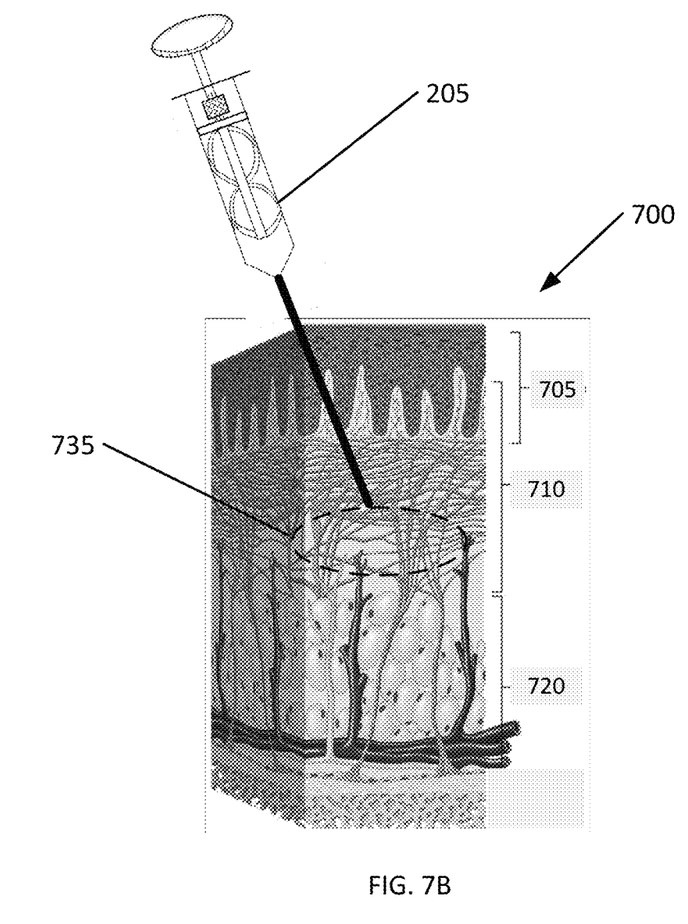
FIG. 7B is a diagram of an example procedure for delivering a cold slurry into the lamina propria of the oral mucosa to tighten the oral mucosa.

FIG. 7B shows another example procedure for tightening the oral mucosa 700 to treat obstructive sleep apnea. In this procedure, a practitioner inserts a cannula of the cold slurry delivery device 205 through the oral epithelium 705 and into the lamina propria 710, i.e., the target tissue. In a convenient example, the procedure is performed using a syringe. The practitioner then delivers a cold slurry from the delivery device 205 to the lamina propria 710. The cold slurry, shown in the figure as delivered cold slurry 735, cools the lamina propria 710, which in turn induces connective tissue production and the lamina propria 710 becomes thicker. As a result, the oral mucosa 700 tightens, and reduces the likelihood of it collapsing while the subject sleeps and causing obstructive sleep apnea.

What is claimed is:

1. A method for mechanically disrupting fibrous tissue strands in cellulite in a subject to improve a cosmetic appearance of the subject's skin, the method comprising:
   identifying a target tissue by imaging,
   delivering a cold slurry from a delivery device to the target tissue, wherein the target tissue is fibrous tissue strands in cellulite, which has a dimpled appearance,
   wherein the cold slurry comprises about 1% to about 75% of ice particles by weight, and
   wherein the ice particles mechanically disrupt the fibrous tissue strands, thereby reducing the dimpled appearance and improving the appearance of the subject's skin.

2. The method of claim 1, further comprising cooling any one of connective tissue, adipose tissue and a combination thereof with the cold slurry, thereby inducing a response that causes the skin to tighten so as to reduce the appearance of wrinkles and lines in the skin.

3. The method of claim 1, further comprising cooling any one of a muscle, a nerve that innervates a muscle, and a combination of a muscle and a nerve that innervates the muscle with the cold slurry temporarily, thereby inhibiting the muscle from contracting so as to reduce the appearance of wrinkles and lines in the skin, which are associated with the muscle contraction.

4. The method of claim 1, further comprising cooling any one of a sebaceous gland, a nerve that innervates a sebaceous gland, and a combination of a sebaceous gland and a nerve that innervates the sebaceous gland with the cold slurry, thereby reducing the activity of the sebaceous gland that causes acne.

5. The method of claim 1, further comprising cooling adipose tissue in cellulite, which has a dimpled appearance, with the cold slurry, thereby inducing apoptosis and reducing the dimpled appearance.

6. The method of claim 1, further comprising delivering the cold slurry to tissue adjacent to the target tissue.

7. The method of claim 1, wherein delivering the cold slurry includes inserting a cannula through the subject's skin, advancing the cannula through connective tissue to the target tissue underlying the connective tissue, and delivering the cold slurry through the cannula to the target tissue.

8. The method of claim 1, wherein delivering the cold slurry includes inserting a cannula through the subject's skin, advancing the cannula to the target tissue, and delivering the cold slurry to the target tissue.

9. The method of claim 1, wherein delivering the cold slurry includes delivering the cold slurry to tissue in one or more areas selected from the group consisting of: around the subject's flanks, abdomen, thigh, upper arm, and submental area under the chin.

10. The method of claim 1, wherein the cold slurry comprises water, salt and glycerol.

11. The method of claim 1, wherein the cold slurry comprises 0.1% to about 20% glycerol and 0.1% to about 20% salt.

12. The method of claim 1, wherein the cold slurry has a mean temperature selected from the group consisting of: about +10° C., about +7° C., about +5° C., about +4° C., about +3° C., about +2° C., about +1° C., about 0° C., about −1° C., about −2° C., about −3° C., about −4° C., about −5° C., about −10° C., about −15° C., about −20° C., about −30° C., about −40° C., and about −50° C.

13. The method of claim 1, wherein the cold slurry comprises spherical or round ice particles with a diameter of about 1 mm to about 0.01 mm.

14. The method of claim 1, further comprising introducing a fluid into a lumen of the delivery device; agitating the fluid within the lumen with an integrated agitation device; and cooling the fluid with a cooling device integrated in the delivery device to generate the cold slurry, wherein delivering the cold slurry includes injecting the cold slurry from the delivery device using a plunger at least partially disposed within the lumen.

15. The method of claim 1, wherein the delivery device comprises a cannula; and
   wherein delivering the cold slurry includes inserting the cannula through the subject's skin, advancing the cannula through connective tissue to the target tissue, and delivering the cold slurry to the target tissue.

16. The method of claim 1, wherein the delivery device comprises a cannula; and
   wherein delivering the cold slurry includes inserting the cannula through the subject's skin, advancing the cannula to the target tissue, and delivering the cold slurry to the target tissue.

17. The method of claim 14, wherein the fluid is agitated while cooling the fluid.

18. The method of claim 14, wherein the cooling device at least partially surrounds the lumen.

* * * * *